United States Patent
McIntosh et al.

(10) Patent No.: US 9,735,773 B2
(45) Date of Patent: Aug. 15, 2017

(54) SYSTEMS AND METHODS FOR SENSING CURRENT THROUGH A LOW-SIDE FIELD EFFECT TRANSISTOR

(71) Applicant: Allegro Microsystems, LLC, Worcester, MA (US)

(72) Inventors: James McIntosh, East Lothian (GB); Robert D. Christie, Fife (GB); Douglas Bryce, Edinburgh (GB); Walter Morrison Stewart Wilson, East Lothian (GB)

(73) Assignee: Allegro Microsystems, LLC, Worcester, MA (US)

( * ) Notice: Subject to any disclaimer, the term of this patent is extended or adjusted under 35 U.S.C. 154(b) by 118 days.

(21) Appl. No.: 14/264,522

(22) Filed: Apr. 29, 2014

(65) Prior Publication Data

US 2015/0311894 A1    Oct. 29, 2015

(51) Int. Cl.
*H02P 1/00* (2006.01)
*H02P 1/28* (2006.01)
(Continued)

(52) U.S. Cl.
CPC ... *H03K 17/6871* (2013.01); *G01R 19/16538* (2013.01); *G01R 19/16571* (2013.01);
(Continued)

(58) Field of Classification Search
CPC ..... A61B 17/1626; B26B 19/00; B26B 19/06; B26B 19/38; B26B 19/388
(Continued)

(56) References Cited

U.S. PATENT DOCUMENTS

| 4,236,832 A | 12/1980 | Komatsu et al. |
| 4,438,347 A | 3/1984 | Gehring |

(Continued)

FOREIGN PATENT DOCUMENTS

| CN | 1501093 A | 6/2004 |
| CN | 101023367 A | 8/2007 |

(Continued)

OTHER PUBLICATIONS

On Semiconductor, "AND8093/D Current sensing Power MOSFETs," URL: http://www.onsemi.com; 12 pages.*

(Continued)

*Primary Examiner* — Kawing Chan
*Assistant Examiner* — Bradley Brown
(74) *Attorney, Agent, or Firm* — Daly, Crowley, Mofford & Durkee, LLP

(57) ABSTRACT

Systems and techniques detecting a reverse current are disclosed. An apparatus comprises a switching circuit coupled to a load and a reference node. The switching circuit may be capable of conducting a reverse current from the reference node to the load when a voltage at the load is lower than a voltage at the reference node. A voltage source has a first terminal coupled to the load, a second terminal configured to follow a voltage at the load, and produces a voltage proportional to a voltage drop across the switching circuit. A comparator circuit is coupled to compare a voltage at the second terminal of the voltage source to the voltage at the reference node and configured to indicate when the reverse current has a magnitude greater than a predetermined threshold.

32 Claims, 5 Drawing Sheets

(51) Int. Cl.
  *H02P 3/00* (2006.01)
  *H02P 7/06* (2006.01)
  *H02P 7/14* (2006.01)
  *H02P 23/00* (2016.01)
  *H02P 25/00* (2006.01)
  *H02P 27/00* (2006.01)
  *H03K 17/687* (2006.01)
  *H02P 31/00* (2006.01)
  *G01R 19/165* (2006.01)
  *H02P 8/12* (2006.01)
  *B26B 19/00* (2006.01)
  *B26B 19/06* (2006.01)
  *A61B 17/16* (2006.01)

(52) U.S. Cl.
  CPC ........... *H02P 8/12* (2013.01); *H02P 31/00* (2013.01); *A61B 17/1626* (2013.01); *B26B 19/00* (2013.01); *B26B 19/06* (2013.01)

(58) Field of Classification Search
  USPC ........................................................ 318/504
  See application file for complete search history.

(56) References Cited

U.S. PATENT DOCUMENTS

| | | | |
|---|---|---|---|
| 4,752,733 A | 6/1988 | Petr et al. | |
| 4,758,943 A | 7/1988 | Aström et al. | |
| 4,760,285 A | 7/1988 | Nelson | |
| 4,767,989 A | 8/1988 | Meyer et al. | |
| 4,823,075 A | 4/1989 | Alley | |
| 4,833,406 A | 5/1989 | Foster | |
| 4,970,411 A | 11/1990 | Halg et al. | |
| 5,247,278 A | 9/1993 | Pant et al. | |
| 5,285,155 A | 2/1994 | Ueda et al. | |
| 5,329,416 A | 7/1994 | Ushiyama et al. | |
| 5,343,143 A | 8/1994 | Voisine et al. | |
| 5,412,255 A | 5/1995 | Wallrafen | |
| 5,424,558 A | 6/1995 | Borden et al. | |
| 5,469,058 A | 11/1995 | Dunnam | |
| 5,517,112 A | 5/1996 | Vig et al. | |
| 5,521,501 A | 5/1996 | Dettmann et al. | |
| 5,621,319 A | 4/1997 | Bilotti et al. | |
| 5,640,090 A | 6/1997 | Furuya et al. | |
| 5,844,140 A | 12/1998 | Seale | |
| 5,936,498 A | 8/1999 | Takeshima et al. | |
| 6,011,770 A | 1/2000 | Tan | |
| 6,211,673 B1 | 4/2001 | Gerber et al. | |
| 6,351,506 B1 | 2/2002 | Lewicki | |
| 6,392,478 B1 | 5/2002 | Mulder et al. | |
| 6,433,545 B1 | 8/2002 | Kunze et al. | |
| 6,436,748 B1 | 8/2002 | Forbes et al. | |
| 6,437,558 B2 | 8/2002 | Li et al. | |
| 6,750,644 B1 | 6/2004 | Berkcan | |
| 6,853,178 B2 | 2/2005 | Hayat-Dawoodi | |
| 6,896,407 B2 | 5/2005 | Nomiyama et al. | |
| 6,917,321 B1 | 7/2005 | Haurie et al. | |
| 7,038,448 B2 | 5/2006 | Schott et al. | |
| 7,190,784 B2 | 3/2007 | Li | |
| 7,259,545 B2 | 8/2007 | Stauth et al. | |
| 7,292,095 B2 | 11/2007 | Burt et al. | |
| 7,319,319 B2 | 1/2008 | Jones et al. | |
| 7,323,870 B2 | 1/2008 | Tatschl et al. | |
| 7,325,175 B2 | 1/2008 | Momtaz | |
| 7,342,761 B2* | 3/2008 | Covault ............... H02H 3/087 361/78 |
| 7,345,470 B2 | 3/2008 | Suzuki | |
| 7,425,821 B2 | 9/2008 | Monreal et al. | |
| 7,474,093 B2 | 1/2009 | Ausserlechner | |
| 7,518,354 B2 | 4/2009 | Stauth et al. | |
| 7,598,601 B2 | 10/2009 | Taylor et al. | |
| 7,605,647 B1 | 10/2009 | Romero et al. | |
| 7,635,993 B2 | 12/2009 | Boeve | |
| 7,694,200 B2 | 4/2010 | Forrest et al. | |
| 7,701,208 B2 | 4/2010 | Nishikawa | |
| 7,729,675 B2 | 6/2010 | Krone | |
| 7,746,056 B2 | 6/2010 | Stauth et al. | |
| 7,746,065 B2 | 6/2010 | Pastre et al. | |
| 7,764,118 B2 | 7/2010 | Kusuda et al. | |
| 7,769,110 B2 | 8/2010 | Momtaz | |
| 7,800,389 B2 | 9/2010 | Friedrich et al. | |
| 7,923,996 B2 | 4/2011 | Doogue et al. | |
| 7,936,144 B2 | 5/2011 | Vig et al. | |
| 7,961,823 B2 | 6/2011 | Kolze et al. | |
| 7,990,209 B2 | 8/2011 | Romero | |
| 8,030,918 B2 | 10/2011 | Doogue et al. | |
| 8,128,549 B2 | 3/2012 | Testani et al. | |
| 8,134,358 B2 | 3/2012 | Charlier et al. | |
| 8,203,329 B2 | 6/2012 | Hohe et al. | |
| 8,447,556 B2 | 5/2013 | Friedrich et al. | |
| 8,542,010 B2 | 9/2013 | Cesaretti et al. | |
| 8,576,589 B2* | 11/2013 | Melanson ............. H02J 7/0054 323/207 |
| 8,680,846 B2 | 3/2014 | Cesaretti et al. | |
| 8,692,546 B2 | 4/2014 | Cesaretti et al. | |
| 2002/0084923 A1 | 7/2002 | Li | |
| 2003/0038675 A1 | 2/2003 | Gailus et al. | |
| 2003/0102909 A1 | 6/2003 | Motz | |
| 2006/0202692 A1 | 9/2006 | Tatschl et al. | |
| 2007/0110199 A1 | 5/2007 | Momtaz et al. | |
| 2007/0247141 A1 | 10/2007 | Pastre et al. | |
| 2007/0285089 A1 | 12/2007 | Ibuki et al. | |
| 2008/0048772 A1 | 2/2008 | Nishikawa | |
| 2008/0094055 A1 | 4/2008 | Monreal et al. | |
| 2008/0110987 A1 | 5/2008 | Cato et al. | |
| 2008/0137784 A1 | 6/2008 | Krone | |
| 2008/0238410 A1 | 10/2008 | Charlier et al. | |
| 2008/0265880 A1 | 10/2008 | Nishikawa | |
| 2008/0278158 A1 | 11/2008 | Granig et al. | |
| 2009/0001964 A1 | 1/2009 | Strzalkowski et al. | |
| 2009/0001972 A1 | 1/2009 | Fernandez et al. | |
| 2009/0033324 A1 | 2/2009 | Tomida et al. | |
| 2009/0085706 A1 | 4/2009 | Baarman et al. | |
| 2009/0212765 A1 | 8/2009 | Doogue et al. | |
| 2009/0237075 A1 | 9/2009 | Koss | |
| 2009/0295350 A1* | 12/2009 | Yamada ............. H02M 3/1588 323/282 |
| 2010/0067152 A1 | 3/2010 | Nakahashi et al. | |
| 2010/0117638 A1 | 5/2010 | Yamashita et al. | |
| 2010/0211347 A1 | 8/2010 | Friedrich et al. | |
| 2010/0301791 A1* | 12/2010 | Watanabe ............. H02M 1/32 318/400.35 |
| 2011/0018533 A1 | 1/2011 | Cesaretti et al. | |
| 2011/0031965 A1 | 2/2011 | Saruki et al. | |
| 2011/0048102 A1 | 3/2011 | Fernandez et al. | |
| 2011/0133723 A1 | 6/2011 | Forsyth et al. | |
| 2011/0298448 A1 | 12/2011 | Foletto et al. | |
| 2012/0016614 A1 | 1/2012 | Hohe et al. | |
| 2012/0112695 A1 | 5/2012 | Nishi et al. | |
| 2012/0274314 A1 | 11/2012 | Cesaretti et al. | |
| 2012/0313635 A1 | 12/2012 | Daubert | |
| 2013/0093412 A1 | 4/2013 | Anelli et al. | |
| 2013/0214774 A1 | 8/2013 | Cesaretti et al. | |
| 2014/0009144 A1 | 1/2014 | Romero | |
| 2014/0312883 A1 | 10/2014 | Friedrich et al. | |

FOREIGN PATENT DOCUMENTS

| | | |
|---|---|---|
| CN | 200986484 Y | 12/2007 |
| DE | 195 39 458 A1 | 4/1997 |
| DE | 196 06 826 A1 | 8/1997 |
| DE | 10 2005 047 413 A1 | 9/2006 |
| DE | 10 2006 037 226 A1 | 2/2008 |
| DE | 10 2007 041 230 B3 | 4/2009 |
| EP | 0 289 414 A2 | 11/1988 |
| EP | 0 289 414 A3 | 11/1988 |
| EP | 0 338 122 | 10/1989 |
| EP | 0 357 013 A2 | 3/1990 |
| EP | 0 357 013 A3 | 3/1990 |
| EP | 1 637 898 A1 | 3/2006 |
| EP | 1637898 | 3/2006 |
| EP | 1637898 A1 | 3/2006 |
| EP | 1 679 524 A1 | 7/2006 |

(56) References Cited

FOREIGN PATENT DOCUMENTS

| | | |
|---|---|---|
| EP | 1 850 143 A1 | 10/2007 |
| GB | 2 276 727 A | 10/1994 |
| JP | A 51-117080 | 10/1976 |
| JP | 61-48777 | 3/1986 |
| JP | S 6148777 A | 3/1986 |
| JP | SHO 61-48777 | 3/1986 |
| JP | S 63-11675 Y2 | 4/1988 |
| JP | H03-176682 | 7/1991 |
| JP | 03-248611 | 11/1991 |
| JP | H03-248611 A | 11/1991 |
| JP | A 06-317637 | 11/1994 |
| JP | 2000-55999 A | 2/2000 |
| JP | 2002-213992 A | 7/2002 |
| JP | 2004-234589 A | 8/2004 |
| JP | 2006-123012 A | 5/2006 |
| JP | 2006-126012 A | 5/2006 |
| JP | A 2006126012 A | 5/2006 |
| JP | 2008-513762 | 5/2008 |
| JP | 2008-513762 A | 5/2008 |
| JP | 2010-500536 A | 1/2010 |
| JP | 4840481 B2 | 1/2011 |
| JP | 2011-052036 A | 3/2011 |
| KR | 10-2007-0060096 A | 6/2007 |
| TW | 200640135 | 11/2006 |
| WO | WO 96/02849 A1 | 2/1996 |
| WO | WO 2004/072672 | 8/2004 |
| WO | WO 2006/035342 A1 | 4/2006 |
| WO | WO 2006/056829 | 6/2006 |
| WO | WO 2007/138508 | 12/2007 |
| WO | WO 2007/138508 A1 | 12/2007 |
| WO | WO 2008/048379 A1 | 4/2008 |
| WO | WO 2008/123144 A1 | 10/2008 |
| WO | WO 2009/002609 | 12/2008 |
| WO | WO 2009/108422 A2 | 9/2009 |
| WO | WO 2009/108422 A3 | 9/2009 |
| WO | WO 2010/096367 A1 | 8/2010 |
| WO | WO 2010/147713 | 12/2010 |
| WO | WO 2011/011479 | 1/2011 |
| WO | WO 2012/001612 | 1/2012 |

OTHER PUBLICATIONS

Letter from Yuasa and Hara dated Mar. 25, 2016; for Japanese Pat. App. No. 2015-013206; 1 page.
Response 2016 with English Claims dated Mar. 17, 2016 to Japanese Office Action; For Japanese Pat. App. No. 2015-013206; 7 pages.
Response filed Apr. 28, 2015; to Office Action dated Jan. 9, 2015; for U.S. Appl. No. 14/321,347; 9 pages.
Japanese Allowed Claims received May 25, 2015; for Japanese Pat. App. No. 2010-547666; 5 pages.
Korean Notice of Allowance with Allowed Claims (English Translation); dated Apr. 20, 2015; for Korean Pat. App. No. 10-2010-7019498; 12 pages.
Notice of Allowance dated Jul. 28, 2015; for U.S. Appl. No. 13/398,127; 22 pages.
Letter to Taiwan International Patent & Law Offices dated Jul. 30, 2014; for Taiwan Pat. App. No. 102102201; 73 pages.
European Response to Search Report received May 23, 2014; for European Patent Application No. EP 12719134.4; 20 pages.
PCT Search Report and Written Opinion of the ISA dated Aug. 4, 2015; for PCT Pat. App. No. PCT/US2015/026071; 16 pages.
Korean Notice of Allowance dated Jul. 31, 2015; for Korean Pat. App. No. 10-2014-7033792; 5 pages.
PCT Search Report and Written Opinion of the ISA dated Aug. 19, 2015; for PCT Pat. App. No. PCT/US2015/026332; 13 pages.
On Semiconductor; "AND8093/D Current Sensing Power MOSFETs;" URL: http://www.onsimi-com/pub_link/Collageral/AND8093-D; 12 pages.
Letter to Yuasa and Hara dated Jun. 19, 2014; for Japanese Pat. App. No. 2012-521746; 4 pages.
Letter from Yuasa and Hara dated Aug. 21, 2014; for Japanese Pat. App. No. 2012-521746; 1 page.
Japanese Argument filed on Jul. 3, 2014; for Japanese Pat. App. No. 2012-521746; 4 pages.
Taiwanese Marked-Up Specification filed on Aug. 28, 2014; for Taiwanese Pat. App. No. 102102201; 72 pages.
European Decision to Grant dated Aug. 14, 2014; for EP Pat. App. No. 13 169 661.9; 7 pages.
PCT International Preliminary Report on Patentability of the ISA dated Aug. 28, 2014, for PCT Pat. App. No. PCT/US2013/021143; 9 pages.
Japanese Notice of Reasons for Rejection dated Sep. 29, 2014; for Japanese Pat. App. No. 2010-547666; 4 pages.
Korean Notice to Submit a Response (with English translation) dated Sep. 30, 2014; for Korean Pat. App. No. 10-2010-7019498; 10 pages.
Letter to Yuasa and Hara dated Aug. 12, 2014; for Japanese application corresponding to PCT Pat. App. PCT/US2013/021143; 2 pages.
Letter from Yuasa and Hara dated Nov. 14, 2014; for Japanese application corresponding to PCT Pat. App. PCT/US2013/021143; 1 pages.
Japanese Claims as filed (English translation) received Nov. 14, 2014; for Japanese application corresponding to PCT Pat. App. PCT/US2013/021143; 8 pages.
Letter to 21$^{st}$ Century Patent & Law Firm (with Amendment from related U.S. case) dated Nov. 18, 2014; for Korean Pat. App. No. 10-2010-701498; 20 pages.
Korean Response to Notice of Reasons for Refusal dated Dec. 1, 2014; for Korean Pat. App. No. 10-2010-701498; 32 pages.
Office Action dated Nov. 24, 2014; for U.S. Appl. No. 13/398,127; 56 pages.
European Decision to Grant a European Patent dated Apr. 23, 2015; for European Pat. App. No. 12719134.4; 2 pages.
U.S. Appl. No. 13/743,451, filed Jan. 17, 2013, Friedrich et al.
Ausserlechner et al.; "Compensation of the Piezo-Hall Effect in Integrated Hall Sensors on (100)-Si;" IEEE Sensors Journal, vol. 7, No. 11; Nov. 2007; ISBN: 1530-437X; pp. 1475-1482.
Ausserlechner et al.; "Drift of Magnetic Sensitivity of Small Hall Sensors Due to Moisture Absorbed by the IC-Package;" Proceedings of IEEE Sensors, 2004; vol. 1; Oct. 24, 2004; ISBN:0-7803-8692-2; pp. 455-458.
Ausserlechner; "Limits of Offset Cancellation by the Principle of Spinning Current Hall Probe;" Proceedings of IEEE Sensors; Oct. 2004; pp. 1117-1120.
Ausserlechner; "The piezo-Hall effect in n-silicon for arbitrary crystal orientation;" Proceedings of IEEE Sensors; vol. 3; Oct. 24, 2004; ISBN: 0-7803-8692-2; pp. 1149-1152.
Bahreyni, et al.; "A Resonant Micromachined Magnetic Field Sensor;" IEEE Sensors Journal; vol. 7, No. 9, Sep. 2007; pp. 1326-1334.
Barrettino, et al.; "CMOS-Based Monolithic Controllers for Smart Sensors Comprising Micromembranes and Microantilevers;" IEEE Transactions on Circuits and Systems-I Regular Papers vol. 54, No.1; Jan. 2007; pp. 141-152.
Baschirotto et al.; "Development and Analysis of PCB Vector 2-D Magnetic Field Sensor System for Electronic Compass;" IEEE Sensors Journal vol. 6, No. 2; Apr. 2006; pp. 365-371.
Bilotti et al.; "Monolithic Magnetic Hall Sensor Using Dynamic Quadrature Offset Cancellation;" IEEE Journal of Solid-State Circuits; vol. 32, Issue 6; Jun. 1997; pp. 829-836.
Blagojevic et al.; "FD SOI Hall Sensor Electronics Interfaces for Energy Measurement;" Microelectronics Journal 37; Sep. 2006; pp. 1576-1583.
Cesaretti et al.; "Effect of Stress Due to Plastic Package Moisture Absorption in Hall Sensors;" IEEE Transactions on Magnets; vol. 45; No. 10; Oct. 2009; pp. 4482-4485.
Demierre, et al.; "Reference Magnetic Actuator for Self-Calibration of a Very Small Hall Sensor Array;" Sensors and Actuators A97-98; Apr. 2002; pp. 39-46.
Frick, et al.; "CMOS Microsystem for AC Current Measurement with Galvanic Isolation;" IEEE Sensors Journal; vol. 3, No. 6; Dec. 2003; pp. 752-760.

(56) References Cited

OTHER PUBLICATIONS

Halg; "Piezo-Hall Coefficients of n-Type Silicon;" Journal of Applied Physics; vol. 64, No. 1; Jul. 1, 1988; pp. 276-282.

Hosticka; "CMOS Sensor Systems;" Sensors and Actuators A66; Apr. 1998; pp. 335-341.

Kanda et al.; "The Piezo-Hall Effect in n-Silicon;" $22^{nd}$ International Conference on the Physics of Semiconductors; vol. 1, Jan. 1995; pp. 89-92.

Kayal et al.; "Automatic Calibration of Hall Sensor Microsystems;" Microelectronics Journal 37; Sep. 2006; pp. 1569-1575.

Krammerer et al.: "A Hall effect sensors network insensitive to mechanical stress;" Proceedings of IEEE Sensors; vol. 3, Oct. 2004; pp. 1071-1074.

Mangnani et al.; "Mechanical Stress Measurement Electronics Based on Piezo-Resistive and Piezo-Hall Effects;" $9^{th}$ International Conference on Electronics, Circuits and Systems 2002; vol. 1; SBN: 0-7803-7596-3; Dec. 2002; pp. 363-366.

Manic et al.; "Short and Long-Term Stability Problems of Hall Plates in Plastic Packages;" IEEE $38^{th}$ Annual International Reliability Physics Symposium; Apr. 2000; pp. 225-230.

Manic; "Drift in Silicon Integrated Sensors and Circuits Due to the Thermo-Mechanical Stresses;" Lausanne, École Polytechnique Fédérale De Lausanne 2000; 176 pages.

Motz et al.; "An Integrated Magnetic Sensor with Two Continuous-Time ΔΣ-Converters and Stress Compensation Capability;" IEEE International Solid-State Circuits Conference; Digest of Technical Papers; Feb. 6, 2006; ISBN: 1-4244-0079-1; pp. 1151-1160.

Motz, et al.; "A Chopped Hall Sensor with Small Jitter and Programmable "True Power-On" Function;" IEEE Journal of Solid-State Circuits; vol. 40, No. 7; Jul. 2005; pp. 1533-1540.

Motz, et al.; "An Integrated Hall Sensor Platforrn Design for Position, Angle and Current Sensing;" IEEE Sensors 2006; Exco, Daegu, Korea / Oct. 22-25, 2006; pp. 1008-1011.

Munter; "A Low-offset Spinning-current Hall Plate;" Sensors and Actuators A21-A23; 1990; pp. 742-746.

Munter; "Electronic Circuitry for a Smart Spinning-current Hall Plate with Low Offset;" Sensors and Actuators A; Jun. 1991;. pp. 747-751.

Partin et al.; "Temperature Stable Hall Effect Sensors;" IEEE Sensors Journal, vol. 6, No. 1; Feb. 2006; pp. 106-110.

Pastre, et al.; "A Hall Sensor Analog Front End for Current Measurement with Continuous Gain Calibration;" IEEE Sensors Journal; vol. 7, No. 5; May 2007; pp. 860-867.

Pastre, et al.; "A Hall Sensor-Based Current Measurement Microsystem With Continuous Gain Calibration;" Research in Microelectronics and Electronics, IEEE vol. 2; Jul. 25, 2005; ISBN: 0-7803-9345-7; pp. 95-98.

Popovic; "Sensor Microsystems;" Proc. $20^{th}$ International Conference on Microelectronics (MWIL 95); vol. 2, NIS, Serbia, Sep. 12-14, 1995; pp. 531-537.

Randhawa; "Monolithic Integrated Hall Devices in Silicon Circuits;" Microelectronics Journal; vol. 12, No. 6; Sep. 14-17, 1981; pp. 24-29.

Ruther et al.; "Integrated CMOS-Based Sensor Array for Mechanical Stress Mapping;" $5^{th}$ IEEE Conference on Sensors, Oct. 2007; pp. 1131-1134.

Ruther et al.; "Theromagnetic Residual Offset in Integrated Hall Plates;" IEEE Sensors Journal; vol. 3, No. 6; Dec. 2003; pp. 693-699.

Sargent; "Switched-capacitor IC controls feedback loop;" EDN; Design Ideas; Feb. 17, 2000; pp. 154 and 156.

Schneider, et al.; "Temperature Calibration of CMOS Magnetic Vector Probe for Contactless Angle Measurement System;" IEDM; Dec. 1996; pp. 533-536.

Schott et al.; "Linearizing Integrated Hall Devices;" 1997 International Conference on Solid-State Sensors and Actuators, Jun. 16-19, 1997; pp. 393-396.

Schott, et al.; "CMOS Single-Chip Electronic Compass with Microcontroller;" IEEE Journal of Solid-State Circuits; vol. 42, No. 12; Dec. 2007; pp. 2923-2933.

Simon et al.; "Autocalibration of Silicon Hall Devices;" $8^{th}$ International Conference on Solid-State Sensors and Actuators; vol. 2; Jun. 25, 1995; pp. 237-240.

Steiner et al.; Offset Reduction in Hall Devices by Continuous Spinning Current Method; Sensors and Actuators A68; 1998; pp. 167-172.

Steiner: "Double-Hall Sensor with Self-Compensated Offset;" Electron Devices Meeting; IDSM '97 Technical Digest; Dec. 7-10, 1997; pp. 911-914.

Stellrecht et al.; Characterization of Hygroscopic Swelling Behavior of Mold Compounds and Plastic Packages; IEEE Transactions on Components and Packaging Technologies, vol. 27, No. 3; Sep. 2004; pp. 499-506.

Trontelj et al; "CMOS Integrated Magnetic Field Source Used as a Reference in Magnetic Field Sensors on Common Substrate;" WEP 1-6; IMTC; May 1994; pp. 461-463.

Tian et al.; "Multiple Sensors on Pulsed Eddy-Current Detection for 3-D Subsurface Crack Assessment;" IEEE Sensors Journal, vol. 5, No. 1; Feb. 2005; pp. 90-96.

Wu, et al.; "A Chopper Current-Feedback Instrumentation Amplifier with a 1mHz 1/f Noise Corner and an AC-Coupled Ripple-Reduction Loop;" IEEE International Solid-State Circuits Conference; Feb. 10, 2009; pp. 322-324.

Zou et al.; "Three-Dimensional Die Surface Stress Measurements in Delaminated and Non-Delaminated Plastic Packages;" 48th Electronic Components and Technology Conference; May 25, 1998; pp. 1223-1234.

Office Action; dated Feb. 2, 2011; for U.S. Appl. No. 12/959,672; 13 pages.

Response filed on May 24, 2011; for Office Action dated Feb. 2, 2011; for U.S. Appl. No. 12/959,672; 8 pages.

Notice of Allowance; dated Feb. 11, 2011; for U.S. Appl. No. 12/037,393; 7 pages.

Office Action dated Jul. 6, 2012; for U.S. Appl. No. 12/706,318, filed on Feb. 16, 2010: 24 pages.

Response filed Sep. 27, 2012; for U.S. Appl. No. 12/706,318; filed on Feb. 16, 2010; 12 pages.

Supplemental Response filed Oct. 12, 2012; for U.S. Appl. No. 12/706,318; filed on Feb. 16, 2010; 12 pages.

Notice of Allowance; dated Dec. 10, 2012; for U.S. Appl. No. 12/706,318; 9 pages.

Office Action dated Jun. 12, 2013; for U.S. Appl. No. 13/743,451; 24 pages.

Response filed Oct. 8, 2013; to Office Action dated Jun. 12, 2013; for U.S. Appl. No. 13/743,451; 12 pages.

Notice of Allowance dated Dec. 24, 2013; for U.S. Appl. No. 13/743,451; 24 pages.

312 Amendment filed Feb. 7, 2014; for U.S. Appl. No. 13/743,451; 7 pages.

Response dated Mar. 21, 2004; to 312 Amendment filed on Feb. 11, 2014; 4 pages.

Office Action dated Sep. 11, 2012 from U.S. Appl. No. 12/840,324, 30 pages.

Response filed Dec. 11, 2012; to Office Action dated Sep. 11, 2012; for U.S. Appl. No. 12/840,324; 15 pages.

Final Office Action dated Feb. 12, 2013; for U.S. Appl. No. 12/840,324; 19 pages.

Response filed May 13, 2013; to Final Office Action dated Feb. 12, 2013; ; for U.S. Appl. No. 12/840,324; 12 pages.

Notice of Allowance; dated May 24, 2013; for U.S. Appl. No. 12/840,324; 12 pages.

Corrected Notice of Allowance; dated Aug. 9, 2013; for U.S. Appl. No. 12/840,324; 6 pages.

Notice of Allowance dated Nov. 14, 2013; for U.S. Appl. No. 13/969,702; 26 pages.

Office Action dated Jun. 11, 2013; for U.S. Appl. No. 13/095,371; 31 pages.

Response filed Sep. 27, 2013; to Office Action dated Jun. 11, 2013; for U.S. Appl. No. 13/095,371; 26 pages.

Notice of Allowance dated Oct. 28, 2013; for U.S. Appl. No. 13/095,971; 19 pages.

Office Action dated Jul. 3, 2014; for U.S. Appl. No. 13/398,127; 73 pages.

(56) References Cited

OTHER PUBLICATIONS

Chinese Office Action; dated Aug. 29, 2012; for Chinese Pat. App. No. 200980106535.4; 4 pages.
Chinese Office Action (Translated into English); dated Aug. 29, 2012; for Chinese Pat. App. No. 200980106535.4; 4 pages.
Chinese Letter from NTD Patent & Trademark Agency Limited; dated Oct. 10, 2012; for Chinese Pat. App. No. 200980106535.4; 13 pages.
Chinese Letter to NTD Patent and Trademark Agency Ltd.; dated Dec. 11, 2012; with instructions to file Response to Official Action; for Chinese Pat. App. No. 200980106535.4; 3 pages.
Chinese Letter from NTD Patent and Trademark Agency Ltd.; dated Jan. 19, 2013; enclosing Response to Official Action; for Chinese Pat. App. No. 200980106535.4; 14 pages.
Chinese Office Action (Engl. Translation) dated Apr. 15, 2013; for CN Pat. App. No. 200980106565.4; 5 pages.
Chinese Letter to NTD Patent and Trademark Agency; dated Jun. 19, 2013; for Chinese Pat. App. No. 200980106535.4; 11 pages.
Chinese Response to Office Action received Jul. 11, 2013; for Chinese Pat. App. No. 200980106535.4; 12 pages.
Chinese Claims from Chinese Office Action dated Nov. 7, 2013 (w/English translation); for Chinese Pat. App. No. 200980106535.4; 8 pages.
Chinese Office Action dated Nov. 7, 2013 (w/English translation); for Chinese Pat. App. No. 200980106535.4; 9 pages.
Chinese Letter to NTD Patent and Trademark Agency, Ltd. dated Dec. 16, 2013; for Chinese Pat. App. No. 200980106535.4; 10 pages.
Chinese Letter from NTD Patent and Trademark Agency, Ltd. dated Jan. 7, 2014; for Chinese Pat. App. No. 200980106535.4; 1 page.
Chinese Response to Office Action received Jan. 7, 2014; for Chinese Pat. App. No. 200980106535.4; 10 pages.
Chinese Notice of Completing Formalities (including English translation) and Search Report dated Mar. 7, 2014; for Chinese Pat. App. No. 200980106535.4; 8 pages.
EP Official Communication; dated Feb. 23, 2012; for EP. Pat. App. No. 10739429.8; 2 pages.
European Response to European Written Opinion; filed on Sep. 4, 2012; for EP Pat. App. No. 10739429.8; 11 pages.
European Decision to Grant a European Patent; dated Sep. 5, 2013; for European Pat. App. No. 10739429.8; 2 pages.
European Search Report; dated Jul. 4, 2013; for EP Pat. App. No. 13169661.9; 2 pages.
European Response filed Mar. 4, 2014; to Official Communication dated Sep. 9, 2013; for European Pat. App. No. 13169661.9; 10 pages.
German Letter to Kuhnen & Wacker dated Jan. 20, 2014, with enclosures; for DE Pat. App. No. 112010000848.5; 14 pages.
German Letter from Kuhen and Wacker dated May 26, 2014 for German Patent Application No. 11 2011 000 848 5 (with claims in English and German) 50 pages.
German Office Action; dated Sep. 23, 2013; for German Pat. App. No. 11 2010 000 848.5; 12 pages.
Japanese Notice of Reasons for Rejection (English translation); dated Apr. 4, 2013; for JP Pat. App. No. 2010-547666; 4 pages.
Japanese Letter from Yuasa & Hara; dated May 27, 2013; for JP Pat. App. No. 2010-547666; 2 pages.
Japanese Response, Argument and Amendment (in Japanese); dated Jul. 3, 2013; for Japanese Pat. App. No. 2010-547666; 6 pages.
Japanese Claims for Argument and Amendment (in English); dated Jul. 3, 2013; for Japanese Pat. App. No. 2010-547666; 5 pages.
Japanese Letter from Yuasa and Hara; dated Oct. 8, 2013; for Japanese Pat. App. No. 2010-547666; 2 pages.
Japanese Notice of Reasons for Rejection (English translation) dated Nov. 26, 2013; for JP Pat. App. No. 2010-547666; 2 pages.
Japanese Notice of Reasons for Rejection dated Mar. 4, 2014; for Japanese Pat. App. No. 2012-5210746; 2 pages.
Japanese Amendment; dated Jun. 12, 2013; for Japanese Pat. App. No. 2012-521746; 5 pages.
Japanese Letter from Yuasa and Hara; dated Aug. 6, 2013; for Japanese Pat. App. No. 2012-521746; 6 pages.
Taiwan Office Action with Taiwan Search Report received Jun. 13, 2014 (English Translation) for Patent Application No. 102102201 14 pages.
PCT International Preliminary Report on Patentability and Written Opinion mailed Sep. 10, 2010 for PCT/US2009/031776.
PCT Search Report and Written Opinion of the ISA for PCT/US2009/031776 dated Oct. 23, 2009.
PCT Search Report and Written Opinion of the ISA for PCT/US2010/024256 dated Aug. 11, 2010.
PCT International Preliminary Report on Patentability and Written Opinion of the ISA for PCT Pat. App. No. PCT/US2010/024256; dated Sep. 1, 2011; 9 pages.
PCT Search Report and Written Opinion of the ISA for PCT/US2010/042694 dated Sep. 27, 2010.
PCT International Preliminary Report on Patentability and Written Opinion of the ISA; dated Feb. 2, 2012; for PCT Pat. App. No. PCT/US2010/042694; 11 sheets.
PCT Search Report and Written Opinion of the ISA for PCT Pat. App. No. PCT/US2012/032315; dated Jun. 22, 2012; 16 pages.
PCT International Preliminary Report on Patentability and Written Opinion of the ISA dated Nov. 7, 2013; for PCT Pat. App. No. PCT/US2012/032315; 13 pages.
PCT Search Report and Written Opinion; dated May 27, 2013; for PCT Pat. App. No. PCT/US2013/021143; 13 pages.
U.S. Pat. No. 7,923,996.
U.S. Pat. No. 8,030,918.
U.S. Appl. No. 12/706,318.
Letter from Yuasa and Hara dated Nov. 24, 2015; For Japanese Pat. App. No. 2014-508370; 3 pages.
Japanese Office Action with English translation and English Claims dated Oct. 23, 2015; For Japanese Pat. App. No. 2014-508370; 16 pages.
Office Action dated Nov. 25, 2015; For U.S. Appl. No. 14/255,166; 58 pages.
Letter from Yuasa and Hara dated Dec. 14, 2015; For Japanese Pat. App. No. 2014-557634; 1 page.
Letter to Yuasa and Hara dated Jan. 9, 2015; for Japanese Pat. App. No. 2010-547666; 6 pages.
Claims filed Jan. 27, 2015 in Response to Japanese Office Action; for Japanese Pat App. No. 2010-547666; 5 pages.
Response dated Feb. 23, 2016 to Office Action dated Nov. 25, 2015; For U.S. Appl. No. 14/255,166; 14 pages.
Response filed Mar. 18, 2015; for Office Action dated Nov. 24, 2014; 28 pages.
European Response filed Mar. 20, 2015; for European Pat. App. No. 13703914.5; 34 pages.
Letter from 21$^{st}$ Century Patent & Law Firm dated Mar. 23, 2015; for Korean Pat. App. No. 10-2014-7033792; 1 page.
Korean Response to Notice of Reasons for Refusal dated Mar. 23, 2015; for Korean Pat. App. No. 10-2014-7033792; 11 page.
Response filed Jul. 30, 2014; of Office Action dated Jul. 3, 2014 for U.S. Appl. No. 13/398,127; 17 pages.
U.S. Appl. No. 14/255,166, filed Apr. 17, 2014, Cessaretti et al.
European Decision to Grant dated Dec. 18, 2014; for European Pat. App. No. 13169661.9; 2 pages.
Letter to Yuasa and Hara dated Dec. 5, 2014; for Japanese Pat. App. No. 2014-508370; 2 pages.
Japanese Claims (English translation) as filed with Request for Examination on Dec. 11, 2014; for Japanese Pat. App. No. 2014-508370; 5 pages.
Notice of Allowance dated Jun. 1, 2015; for U.S. Appl. No. 14/321,347; 10 pages.
Korean Notice to Submit a Response dated Sep. 30, 2014; for Korean Pat. App. No. 10-2010-7019498; 5 pages.
European Notice of Allowance dated Aug. 29, 2014; for European Pat. App. No. 12 719 134.4; 7 pages.
Taiwan Notice of Allowance dated Sep. 26, 2014; for Taiwan Pat. App. No. 102102201; 2 pages.
Allegro MicroSystems, LLC; A3981 Automotive, Programmabe Stepper Driver; datasheet; Jan. 2013; 43 pages.

(56) References Cited

OTHER PUBLICATIONS

Office Action dated Jan. 9, 2015; for U.S. Appl. No. 14/321,347; 29 pages.
Letter from Yuasa and Hara dated Feb. 1, 2016; For Japanese Pat. App. No. 2014-508370; 1 page.
Letter from Yuasa and Hara dated Jan. 28, 2016; For Japanese Pat. App. No. JP 2015-013206; 3 pages.
Japanese Notice of Reasons for Rejection dated Jan. 4, 2016; For Japanese Pat. App. No. 2015-013206; 7 pages.
Response filed Mar. 2, 2015; to Office Action dated Oct. 30, 2014; for U.S. Appl. No. 13/177,075; 16 pages.
Korean Notice to Submit a Response dated Jan. 30, 2015; for Korean Pat. App. No. 5-2002-043492-2; 6 pages.
Letter to 21$^{st}$ Century Patent & Law Firm dated Mar. 10, 2015; for Korean Pat. App. No. 10-2014-7033792: 2 pages.
Response to Notice of Appeal with English Claims filed Sep. 26, 2016 for Japanese Application No. 2014-508370; 18 pages.
On Semiconductor, "AND8093/D Current Sensing Power MOSFETs", Jul. 2002; pp. 1-12.
Taiwanese Search Report (with English translation) dated Aug. 2, 2016; for Taiwanese Pat. App. No. 104111440; 2 pages.
Taiwanese Office Action (with English translation) dated Sep. 5, 2016; for Taiwanese Pat. App. No. 104111440; 26 pages.
Letter from Japanese Associate dated Sep. 27, 2016 indicating Notice of Appeal filed in Japan and enclosing Current Claims dated Aug. 29, 2016; for Japanese Patent Application No. 2015-013206; 3 pages.
Letter from Yuasa and Hara dated Jun. 23, 2016; For Japanese Pat. App. No. JP 2014-508370; 3 pages.
Japanese Office Action dated May 27, 2016; For Japanese Pat. App. No. JP 2014-508370; 5 pages.
Claims on File dated Jun. 23, 2016; For Japanese Pat. App. No. JP 2014-508370; 5 pages.
Korean office Action (with English translation dated May 17, 2016 for Korean application No. 10-2012-7004427; 28 Pages.
Request for Continued Examination and Response to Final Office Action dated Jun. 23, 2016 filed on Sep. 12, 2016 for U.S. Appl. No. 14/255,166; 17 pages.
The Korean Intellectual Property Office Notice of Allowance (w/ English Translation) and Allowed Claims dated Sep. 22, 2016 related to Korean Patent Application No. 10-2012-7004427; 10 Pages.
Notice of Reason for Rejection and Claims Now on File from Japanese Patent Office dated Sep. 20, 2016; regarding Japanese Patent Application No. 2014-557634; 12 pages.
PCT International Preliminary Report for PCT Application No. PCT/US2015/026071 dated Oct. 27, 2016; 13 pages.
Final Office Action dated Jun. 23, 2016 corresponding to U.S. Appl. No. 14/255,166; 31 Pages.
Letter to 21$^{st}$ Century dated Jul. 7, 2016 2016 for Korean Patent Application No. 10-2012-7004427; 5 pages.
Letter from 21$^{st}$ Century dated Jul. 15, 2016 for Korean Patent Application No. 10-2012-7004427; 1 page.
Response (w/ English translation) filed Jul. 15, 2016 to Korean Office Action dated May 17, 2016 for Korean Patent Application No. 10-2012-7004427; 38 pages.
Letter from Yuasa and Hara dated Dec. 14, 2016 regarding Appeal for JP Pat App. No. 2015-013206; 3 pages.
Translation of Current Claims on the file (as amended on Aug. 29, 2016) for JP 2015-013206; 2 pages.
PCT International Preliminary Report on Patentability for Application No. PCT/US2015/026332 dated Nov. 10, 2016; 10 pages.
Response to Taiwanese Office Action with English Claims filed Dec. 6, 2016 for Taiwanese Application No. 104111440; 33 pages.
Translation of Examiner's Pre-Trial Report filed re: Yuasa and Hara Letter dated Jan. 13, 2017 for JP Pat. Appl. No. 2014-508370; 5 pages.
Claims Now on File for re; Yuasa and Hara Letter dated Jan. 13, 2017 for JP Pat. Appl. No. 2014-508370; 5 pages.
Taiwanese Office Action (with English translation) dated Jan. 19, 2017 including Search Report; for Taiwanese Pat. App. No. 104111440; 27 pages.
English Translation of Report of Re-Examination before Appeal dated Nov. 28, 2016 for JP Appl. No. 2015-013206; 3 pages.
Letter to Yuasa and Hara dated Feb. 17, 2017 for JP Pat. Appl. No. 2015-013206; 3 pages.
Letter from Yuasa and Hara dated Dec. 8, 2016 regarding Japanese Pat. Appl. No. 2014-557634; 1 page.
Claims now on file for Japanese Pat. Appl. No. 2014-557634 filed with the Japanese Patent Office on Nov. 22, 2016; 9 pages.
Allowed Claims from Yuasa and Hara Allowance Report Letter dated Mar. 28, 2017 for JP Pat. Appl. No. 2014-557634; 9 pages.
Supplemental Amendment filed on Dec. 19, 2016 for U.S. Appl. No. 14/255,166; 11 pages.
Notice of Allowance dated Jan. 4, 2017 for U.S. Appl. No. 14/255,166; 25 pages.
"CMOS-Based Monolithic Controllers for Smart Sensors Comprising Micromembranes and Microantilevers", Barrettino et al.; IEEE Transaction on Circuits and Systems—I. Regular Papers., vol. 54, No. 1, Jan. 2007; 12 pages.
Government of India, Patent Office Examination Report dated Mar. 6, 2017; 8 pages.
Letter to Yuasa and Hara regarding Appeal dated Feb. 7, 2017 for JP Pat. Appl. No. 2014-508370; 5 pages.
Letter from Yuasa and Hara regarding Appeal dated Feb. 20, 2017 for JP Pat. Appl. No. 2014-508370; 1 page.
Revised Claims for Appeal dated Feb. 7, 2017 for JP Pat. Appl. No. 2014-508370; 6 pages.
Official Communication filed on May 12, 2017 for EP Pat. Appl. No. 15719938.1; 3 pages.
Amended claims filed on May 12, 2017 for EP Pat. Appl. No. 15719938.1; 5 pages.
Allowed claims filed on Jun. 5, 2017 for JP Pat. Appl. No. 2015-013206; 2 pages.
Allowed Claims filed with Allowance Report received Jun. 2, 1017 for JP Pat. Appl. No. 2014-508370; 5 pages.

* cited by examiner

SYSTEMS AND METHODS FOR SENSING CURRENT THROUGH A LOW-SIDE FIELD EFFECT TRANSISTOR

FIELD

This disclosure relates to current sensing and, more particularly, to sensing current through a low-side field effect transistor ("FET").

BACKGROUND

There are an increasing number of applications that require current sensing and current regulation with inductive loads. These applications include, but are not limited to: switching motor drivers, voltage regulators, and rectifying circuits and systems.

Switching applications such as these often employ an H-bridge or half-bridge to drive the inductive load. In certain applications, the system attempts to halt or reverse the direction of current though the inductive load by switching transistors in the bridge on and off. This can cause a so-called fly-back effect to occur, where current through the inductive load cannot change direction instantaneously, causing a phase discrepancy between the switching bridge (which may effectively provide alternating power to the load) and the current through the load. Immediately after switching, the fly-back effect can cause a reverse current to flow from ground, through the low side transistors, to the load.

Phase discrepancies and the fly-back effect can lead to imprecision in controlling the load. For instance, in the case of a motor controller, phase discrepancies can cause imprecision in controlling the motor. In the case of a voltage regulator or rectifier, phase discrepancies can create unwanted voltage or current levels in the output. Thus, some systems attempt to regulate fly-back voltage and current to minimize their effect. To do so, some systems monitor and detect fly-back current that flows in a reverse direction through the low side transistors of the H-bridge or half-bridge.

SUMMARY

In an embodiment, an apparatus comprises a switching circuit coupled to a load and a reference node. The switching circuit may be capable of conducting a reverse current from the reference node to the load when a voltage at the load is lower than a voltage at the reference node. A voltage source has a first terminal coupled to the load, a second terminal configured to follow a voltage at the load, and produces a voltage proportional to a voltage drop across the switching circuit. A comparator circuit is coupled to compare a voltage at the second terminal of the voltage source to the voltage at the reference node and configured to indicate when the reverse current has a magnitude greater than a predetermined threshold (i.e., when a predetermined reverse current flows).

In another embodiment, a motor driver circuit comprises a low-side transistor coupled between a load and a reference node. The low-side transistor is capable of conducting a reverse current from the reference node to the load when a voltage at the load is lower than a voltage at the reference node. A voltage source has a first terminal coupled to the load, a second terminal configured to follow a voltage at the load, and a produced voltage proportional to a voltage drop across a body diode of the low-side transistor. A comparator circuit coupled to compare a voltage at the second terminal of the voltage source to the voltage at the reference node and configured to indicate when the reverse current is flowing.

In another embodiment, a motor driver circuit includes a motor and a switched bridge for driving the motor. The bridge includes a low-side transistor having a gate terminal coupled to a control circuit, a drain terminal coupled to at least one coil of the motor, and a source terminal coupled to a reference node. A sense transistor has a gate terminal coupled to the gate terminal of the low-side transistor, a drain terminal coupled to the at least one coil of the motor, and a source terminal. A current source is coupled to the source terminal of the sense transistor to produce a voltage across a body diode of the sense transistor and to allow a voltage at the source terminal of the sense transistor to follow a voltage at the at least one coil of the motor. A comparator circuit is coupled to compare the voltage at the source terminal of the sense transistor to a voltage at the reference node and to indicate when a predetermined reverse current is flowing from the reference node to the at least one coil of the motor through the low-side transistor by indicating when the voltage at the source terminal of the sense transistor is less than the voltage at the reference node.

A method includes generating, by a voltage source, a voltage that is proportional to a voltage drop across a switching circuit that is coupled to a load and a reference node. At least one terminal of the voltage source is allowed to follow a voltage at the load. An indication as to whether a predetermined reverse current is flowing through the switching circuit is provided, by comparing a voltage at the one terminal of the voltage source to a voltage at the reference node.

BRIEF DESCRIPTION OF THE DRAWINGS

The foregoing features may be more fully understood from the following description of the drawings. The drawings aid in explaining and understanding the disclosed technology. Since it is often impractical or impossible to illustrate and describe every possible embodiment, the provided figures depict one or more exemplary embodiments. Accordingly, the figures are not intended to limit the scope of the invention. Like numbers in the figures denote like elements.

DETAILED DESCRIPTION

In the following description, the term "on", when referring to a transistor, refers to a transistor state that allows current to flow through the transistor. Examples of an "on" state include, but are not limited to: a saturation state, an active state, and the like. The term "off", when referring to a FET, refers to a transistor state that minimizes current flow through the transistor. Examples of an "off" state include, but are not limited to, a cutoff state and the like.

Figure 1:
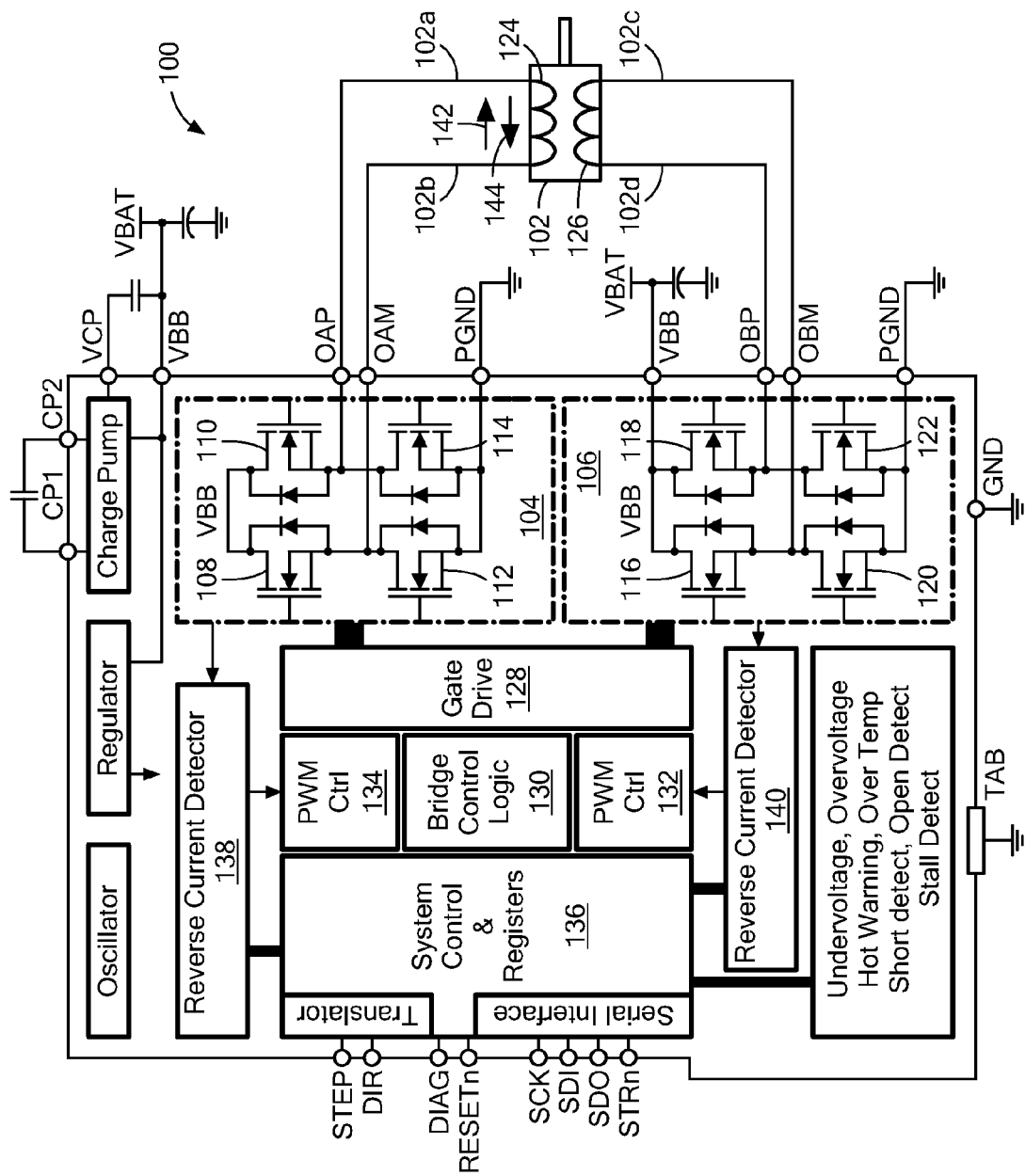
FIG. 1 is a block diagram of a system for detecting reverse current.

Referring to FIG. 1, a system 100 is coupled to a load 102 to electrically drive the load. In an embodiment, system 100 is a motor driver circuit and load is a motor 102 having one or more inductive windings 124 and 126. In an embodiment, motor 102 is a stepper motor and system 100 is a stepper motor controller. In other embodiments, system 100 may be another type of circuit and motor 102 may be another type of load. For example, system 100 may be a switching voltage regulator and the load may be circuitry or devices powered by the switching voltage regulator. In yet another embodiment, system 100 may be a switching rectifier.

As shown, system 100 includes one or more H-bridge circuits 104 and 106 coupled to inputs of motor 102. H-bridge circuit 104 includes two high-side field effect transistors ("FETs") 108 and 110 and two low side FETs 112 and 114. FETs 108, 110, 112, and 114 may be viewed as switches that provide power to motor 102. Signal 102a is coupled to and driven by FETs 110 and 114, and signal 102b is coupled to and driven by FETs 108 and 112, as shown. In an embodiment, signal 102a is coupled to one side of a motor winding 124 in motor 102 and signal 102b is coupled to the other side of motor winding 124 in motor 102.

H-bridge circuit 106 includes two high side FETs 116 and 118 and two low side FETs 120 and 122. FETs 116, 118, 120, and 122 may be viewed as switches that provide power to motor 102. Signal 102c is coupled to and driven by FETs 116 and 120 and signal 102d is coupled to and driven by FETs 118 and 122. In an embodiment, signal 102c is coupled to one side of a motor winding 126 in motor 102 and signal 102d is coupled to the other side of motor winding 126 in motor 102.

In embodiments, H-bridge circuit 104 and/or H-bridge circuit 106 may be replaced by half-bridge circuits, having a single high-side and a single low-side FET. The half bridge circuit may be coupled to one side of the motor winding, with the other side of the motor winding coupled to either a power source or ground.

System 100 also includes additional circuits for controlling operation of H-bridges 104 and 106, and thus for controlling motor 124. As shown, system 100 includes a gate drive circuit 128 which may be coupled to the gate terminals of FETs 108-122 to control the operation of the FETs. A bridge control logic circuit 130 and PWM controller 134 provide timing and control circuitry for controlling motor 102. For example, bridge control logic circuit 130 may control direction, speed, or position of motor 102.

System 100 may also include system control and register circuit 136. System control and register circuit 136 may include inputs such as STEP input, to instruct system 100 to advance a stepper motor by one step (or a half-, quarter-, or eighth-, or sixteenth-step), a DIR input to control the direction of rotation of motor 102, a RESET input, a clock input, a serial interface, etc. Registers within system control and register circuit 136 may, for example, be programmed via the serial interface. The programmable registers may also control operation of the system, and may include programmable control registers that affect operation of system 100 including but not limited to: registers to control rectification, blank time, frequency, dither control, slew rate, max phase current, motor step resolution (e.g. full-, half-, quarter-, or eighth-, or sixteenth-step resolution), serial communication parameters, and/or other operating parameters of system 100.

In embodiments, system 100 is capable of driving motor 102, e.g. a stepper motor, in full-, half-, quarter-, eighth-, and sixteenth-step modes, with phase current up to about +/−1.4 Amps. PWM control circuits 132 and 134 control the phase current by controlling the driving of the gates of FETs 108-122 using pulse-width modulation techniques.

System 100 also includes reverse current detector circuits 138 and 140 to detect when current is flowing in a reverse direction, i.e. from ground to motor 102, through low-side FETs 112, 114, 120, or 122. The reverse current detector circuits may indicate when a reverse current flows through the low side FETs, which will be discussed below in greater detail.

System 100 may also include other circuits, such as oscillators, regulators, charge pumps, under-voltage and over-voltage detection circuits, temperature sensing circuits, etc.

In operation, system 100 controls motor 102 by switching FETs 108-122 on and off. For example, referring to H-bridge 104, system 100 may turn FETs 108 and 114 on (i.e. place FETs 108 and 114 in a conducting state) and turn FETs 110 and 112 off (i.e. place FETs 110 and 112 in a non-conducting state). This allows current to flow from power source VBB, through FET 108, through motor winding 124 in the direction of arrow 142, through FET 114, and finally to ground. System 100 may then turn FETs 108 and 114 off and turn FETs 110 and 112 on. This allows current to flow in the opposite direction through motor winding 124: from power source VBB, though transistor 110, through motor winding 124 in the direction of arrow 144, through FET 112, and finally to ground. System 100 may switch FETs 116-122 of H-bridge 106 in the same or a similar manner to drive current through motor winding 126.

One skilled in the art will recognize that, if motor 102 is a two-phase stepper motor, alternating the current through windings 124 and 126 will cause motor 102 to rotate. By controlling the timing of the current switching, system 100 can control the speed, direction, and position of motor 102. However, as noted above, system 100 may be used to control other types of loads including, but not limited to, other types of electric motors, regulated voltage loads, etc.

Because the motor coils are inductive, attempting to instantaneously switch the direction of the current quickly can cause fly-back voltage and/or fly-back current. Consider the situation where FETs 108 and 114 are closed and current is flowing through motor coil 124 in the direction of arrow 142. In this situation, the voltage of signal 102b will be relatively high (e.g. near VBB) and the voltage of signal 102a will be relatively low (e.g. near ground). When FETs 108 and 114 open and FETs 110 and 112 close, the voltage at signal 102b approaches ground and the voltage at signal 102a approaches VBB. However, due to the inductance of coil 124, the current through coil 124 will not change directions instantaneously—it will continue to flow in the direction of arrow 142 immediately after the FETs are switched. This can drive the voltage level of signal 102a up, potentially to a level greater than the voltage at VBB, and/or drive the voltage level of signal 102b down, potentially to a level lower than the ground voltage. If the voltage at signal 102b is less than the ground voltage, a reverse current may flow from ground, through FET 114, to motor coil 124 of motor 102.

Fly-back voltage and current effects of the motor can cause inaccuracies and inefficiencies in system operation. For example, the fly-back effects can affect the shape of the current waveform and/or the phase of current through the motor winding, which can create imprecision in controlling the motor and cause energy to be lost in the form of heat. Therefore, system 100 may include circuitry to minimize the effect of the fly-back voltage and/or current of the inductive motor coil. In embodiments, PWM control circuits 132 and 134 may act to minimize the time during which reverse current is flowing from ground, through the low side FETs, to the motor winding. The PWM control circuits may employ a fast decay, slow-decay, and/or a mixed mode scheme to minimize the fly-back current.

A fast-decay scheme switches the FETs in an H-bridge as described above. For example, referring to H-bridge 104, a fast-decay scheme will switch between driving FETs 108 and 114 open and driving FETs 110 and 112 closed, to driving FETs 108 and 114 closed and driving FETs 110 and 112 open. This will cause the fly-back current to decay at a relatively fast rate because the H-bridge will be driving current in the opposite direction during the fly-back current.

A slow-decay scheme ties both sides of the motor winding to ground or ties both sides of the motor winding to the power supply (e.g. VBB) after the coil has been turned off. Thus, between driving current through the motor coil in the direction of arrow 142 and driving current through the motor coil in the direction of arrow 144, the system 100 may turn on both low-side FETs (e.g. FETs 112 and 114), and turn off both high-side FETs (e.g. FETs 108 and 110) to tie both sides of the motor winding to ground; or may turn off both low-side FETs and turn on both high-side FETs to tie both sides of the motor winding to VBB to allow the fly-back current to decay. This ties both ends of the motor winding 124 to ground to allow the fly-back current to decay at a relatively slower rate than when using fast-decay.

A mixed-mode decay uses both fast-decay and slow-decay schemes. Under mixed-mode, after driving current through the motor in the direction of arrow 142, the system 100 may immediately employ a fast-decay scheme by switching the FETs 108-114 to drive the current in the opposite direction (i.e. in the direction of arrow 144). After the fly-back current has been partially reduced by the fast-decay, the system 100 may then employ a slow-decay scheme by turning FETs 112 and 114 on to tie both ends of motor winding 124 to ground. System 100 may then drive motor winding in either direction 142 or 144 to control motor 102.

To determine when reverse current is flowing through the low side FETs, so that PWM control circuits can control the decay of fly-back current, reverse current detector circuits 138 and 140 may detect the reverse current flowing through the low-side FETs.

Figure 2:
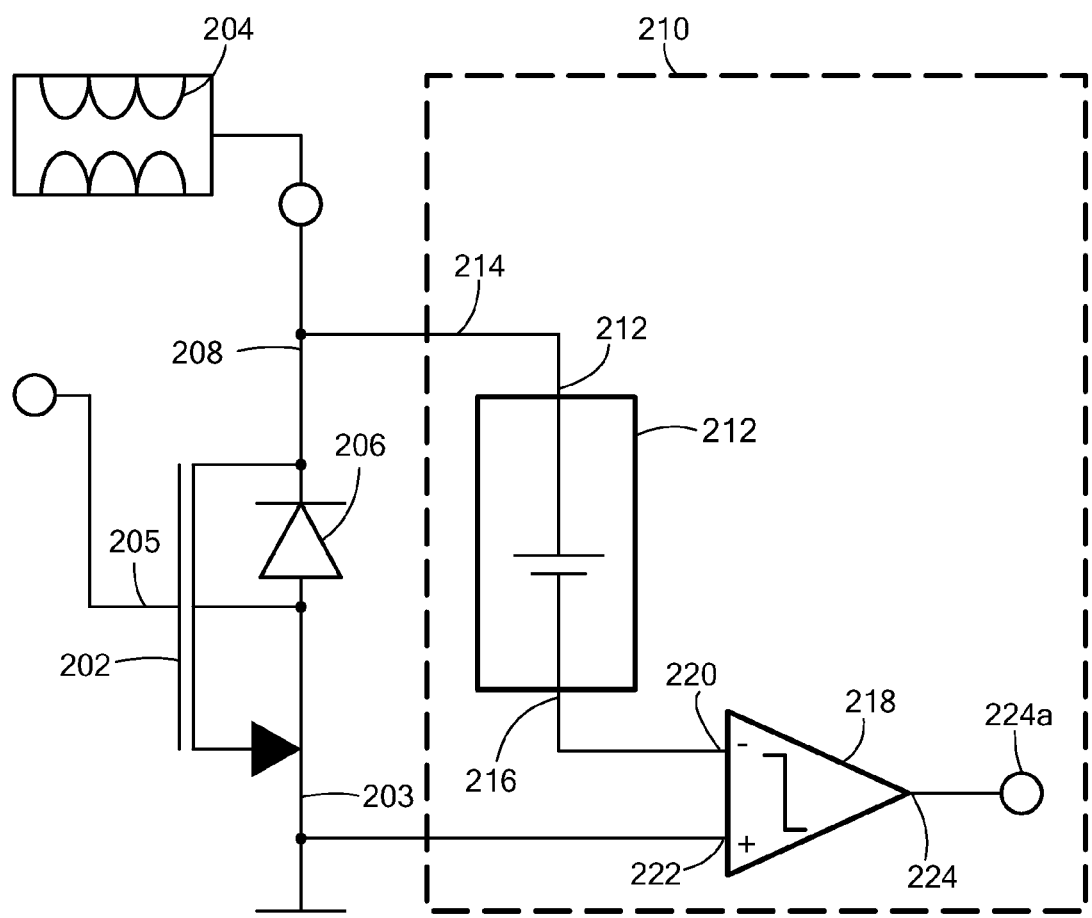
FIG. 2 is a block diagram of a reverse current detector circuit.

Referring to FIG. 2, a switching circuit (e.g. FET 202) is coupled to a load (e.g. motor 204) and a reference node (e.g. ground 203). FET 202 may be the same as or similar to low-side FETs 112, 114, 120, and/or 122 in FIG. 1. FET 202 may be capable of conducting a reverse current from the reference node to the load (i.e. from ground to motor 204) when a voltage at the load is lower than a voltage at the reference node. For example, FET 202 may include a body diode 206 through which current can flow when the voltage at drain terminal 208 is lower than the ground voltage. The gate terminal 205 of FET 202 may be coupled to and driven by a gate drive circuit, such as gate drive circuit 128 in FIG. 1.

A reverse current detector circuit 210 may include a voltage source circuit 212 having a first terminal 214 coupled to the load, a second terminal 216 configured to follow a voltage at the load. Reverse current detector circuit 210 may be the same as or similar to reverse current detector circuit 138 and/or reverse current detector circuit 140 in FIG. 1.

Voltage source circuit 212 may produce a voltage proportional to a voltage drop across the switching circuit. For example, voltage source circuit 212 may produce a voltage approximately proportional or equal to a voltage across body diode 206 when current is flowing through body diode 206.

A comparator circuit 218 has a first input 220 coupled to receive the voltage at second terminal 216 and another input 222 coupled to receive the voltage at the reference node 203. Thus, comparator circuit 218 may compare a voltage at the second terminal 216 of the voltage source circuit 212 to the voltage at the reference node 203. Comparator circuit 218 also includes an output terminal 224 which produces a signal 224a to indicate when the reverse current through FET 202 has a magnitude greater than a predetermined threshold (i.e. when a predetermined reverse current flows). For example, when the voltage at terminal 216 drops below the voltage at reference node 203, comparator circuit 218 asserts signal 224a to indicate that reverse current is flowing through FET 202. One of skill in the art will recognize that the comparator may be configured to produce positive logic (i.e. a high output indicating when a predetermined reverse current is flowing) or negative logic (i.e. a low output indicating when a predetermined reverse current is flowing).

Figure 3:
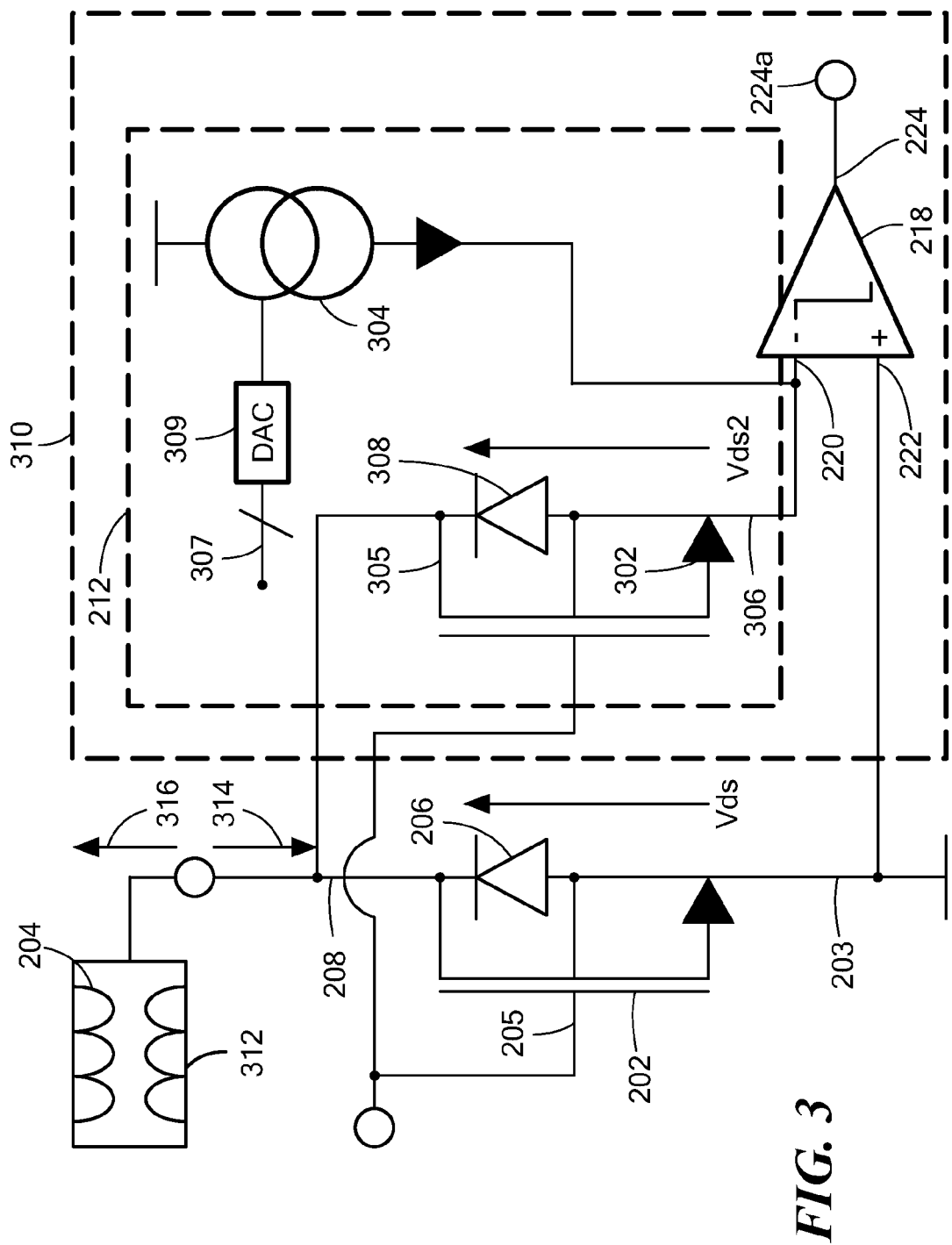
FIG. 3 is a block diagram of a reverse current detector circuit.

Referring to FIG. 3, a reverse current detector circuit 310 may be the same as or similar to reverse current detector circuit 210 in FIG. 2. As shown in FIG. 3, voltage source circuit 212 may comprise a sense transistor (i.e. FET 302) and a current source 304. A first terminal (e.g. drain terminal 305) of FET 302 is coupled to the load 204, and a second terminal (e.g. source terminal 306) of FET 302 is coupled to input 220 of comparator circuit 218, and allowed to follow the voltage at the load 204. The gate terminal of FET 302 may be tied to the gate terminal of FET 202 so that FETs 202 and 302 are turned on and off at the same time.

As shown, FET 302 may include a body diode 308. In an embodiment, the conduction threshold voltage of body diode 308 may be about the same as the conduction threshold voltage of body diode 206, so that the voltage drop across body diode 308 when a predetermined reverse current is flowing through FET 302 is about the same as the voltage drop across body diode 206 when the predetermined reverse current is flowing through FET 202.

The conduction threshold voltage of body diode 308 and/or body diode 206 may be between about 0.3V to about 0.8V. In embodiments, the conduction threshold voltage may be up to 1.4V or higher. In other embodiments, the conduction threshold voltage of body diode 308 may be different than the threshold voltage of body diode 206.

FET 302 may be proportionally smaller than FET 202. For example, if FETs 202 and 302 are part of an integrated circuit, FET 302 may comprise a smaller area on the silicon than FET 202. In embodiments, the area of FET 302 may be on the order of about 1000 to 1400 times smaller than that of FET 202. Thus, the reverse current through FET 302 may need only be about 1000 to about 1400 times less than the reverse current through FET 202 in order to produce a proportional voltage drop (e.g. a substantially equal voltage drop) across body diode 308 to that of the voltage drop across body diode 206.

In embodiments, current source 304 is a variable current source, such as may be a digital-to-analog controlled current source, or by be controlled with a digital-to-analog converter. For example, current source 304 may have a digital input 307. Digital input 307 may be a digital bus that can control the magnitude of the current produced by current source 304. In an embodiment, digital input 307 is a 16-bit digital bus.

Current source 304 may drive a variable current into source terminal 310 of FET 302, through body diode 308, and into load 204. Reverse current through low-side FET 202 acts to discharge the fly-back current of motor 204. Although the reverse current through FET 302 is smaller than the reverse current through FET 202, the reverse current through FET 202 may also contribute to discharging the fly-back current.

In operation, reverse current detector circuit 310 detects reverse current flowing from reference node 203, through FET 202, and into motor 204. While the reverse current is flowing, and more particularly, while the magnitude of the reverse current exceeds a predetermined threshold (i.e. when a predetermined reverse current flows), comparator circuit 218 asserts signal 224a to indicate that the predetermined reverse current is flowing.

First consider the situation where the predetermined threshold is zero. In other words, reverse current detector circuit 310 is configured to assert signal 224a when any reverse current is flowing through FET 202. In this situation, current source 304 is configured to drive a current through body diode 308 so that the voltage drop across body diode 308 is substantially equal to the conduction threshold of body diode 206. Assume also that the first terminal 208 is coupled to one side of motor winding 312.

While driving motor 204 with low-side FET 202 on, current flows through winding 312, through FET 202, to reference node 203. Because FET 202 is in saturation, the voltage at terminal 208 is Vds, which may be zero or very close to zero. Assuming that reference node 203 is a ground node, voltage at terminal 208 is zero or very close to zero.

When low-side FET switches off, the instantaneous current through the inductive winding 312 continues to flow in the direction of arrow 314, which drives the voltage at terminal 208 down. If the voltage at terminal 208 drops to a level so that the voltage across body diode 206 meets or exceeds the conduction threshold of body diode 206, then reverse current will flow from reference node 203, through body diode 206, toward motor 204, in the direction of arrow 316.

Recall that current source 304 is driving a predetermined current through FET 302 so that the voltage drop across body diode 308 is substantially equal to the conduction threshold of body diode 206. In other words, voltage Vds2 is substantially equal to voltage Vds. Thus, when body diode 206 is on the verge of conducting reverse current, the voltage at source terminal 306 is substantially equal to the voltage at reference node 203.

If the voltage at terminal 208 is driven further down by the fly-back current, body diode 206 will begin to conduct reverse current. Also, as the voltage at terminal 208 is driven further down, the voltage at source terminal 306 will follow the voltage at terminal 208 so that, as body diode 206 begins to conduct, the voltage at source terminal 306 will drop below the voltage at reference node 203. When the voltage at source terminal 306 drops below the voltage at reference node 203, comparator circuit 218 will assert signal 224a to indicate that reverse current is flowing through FET 202.

Changing the output of current source 304 can change the predetermined threshold of reverse current through FET 202 that must be exceeded in order for the comparator 208 to assert signal 224a. As noted above, current source 304 may be a variable current source. In one embodiment, current source 304 may be, or may be controlled by, a 16-bit DAC such as DAC 309, for example.

The example above illustrates operation of reverse current detector circuit 310 where the predetermined threshold of reverse current being detected is zero or, in other words, where signal 224a is asserted as soon as reverse current flows through FET 202. However, reverse current detector 310 can be configured to assert signal 224a only if the magnitude of the reverse current exceeds other predetermined thresholds. In embodiments, this can be accomplished by increasing the current provided by current source 304. If the output of current source 304 is increased, the voltage across body diode 308 will proportionally increase. Therefore, in order to trip the comparator circuit 218, the voltage at terminal 208 must be driven to a relatively lower voltage than in the zero-threshold example above, which correlates to a relatively higher reverse current through flowing through body diode 206 prior to the comparator circuit 218 asserting output signal 224a. Alternatively, the output current of current source 304 can be decreased so that signal 224a is asserted when the voltage at terminal 208 drops to a level that does not yet allow reverse current to flow through body diode 206. In an embodiment, the current provided by current source 304 can be configured so that comparator circuit 218 trips when the reverse current has a magnitude between about 0 Amps and about 1400 milliamps.

It will be appreciated that while adjusting the current provided by current source 304 as described above is one way to adjust the level of reverse current necessary to cause the comparator circuit 218 to trip, an offset voltage may be introduced between the reference node 203 and the comparator input 222. Such an embodiment may incorporate a programmable offset into the comparator circuit.

Figure 4:
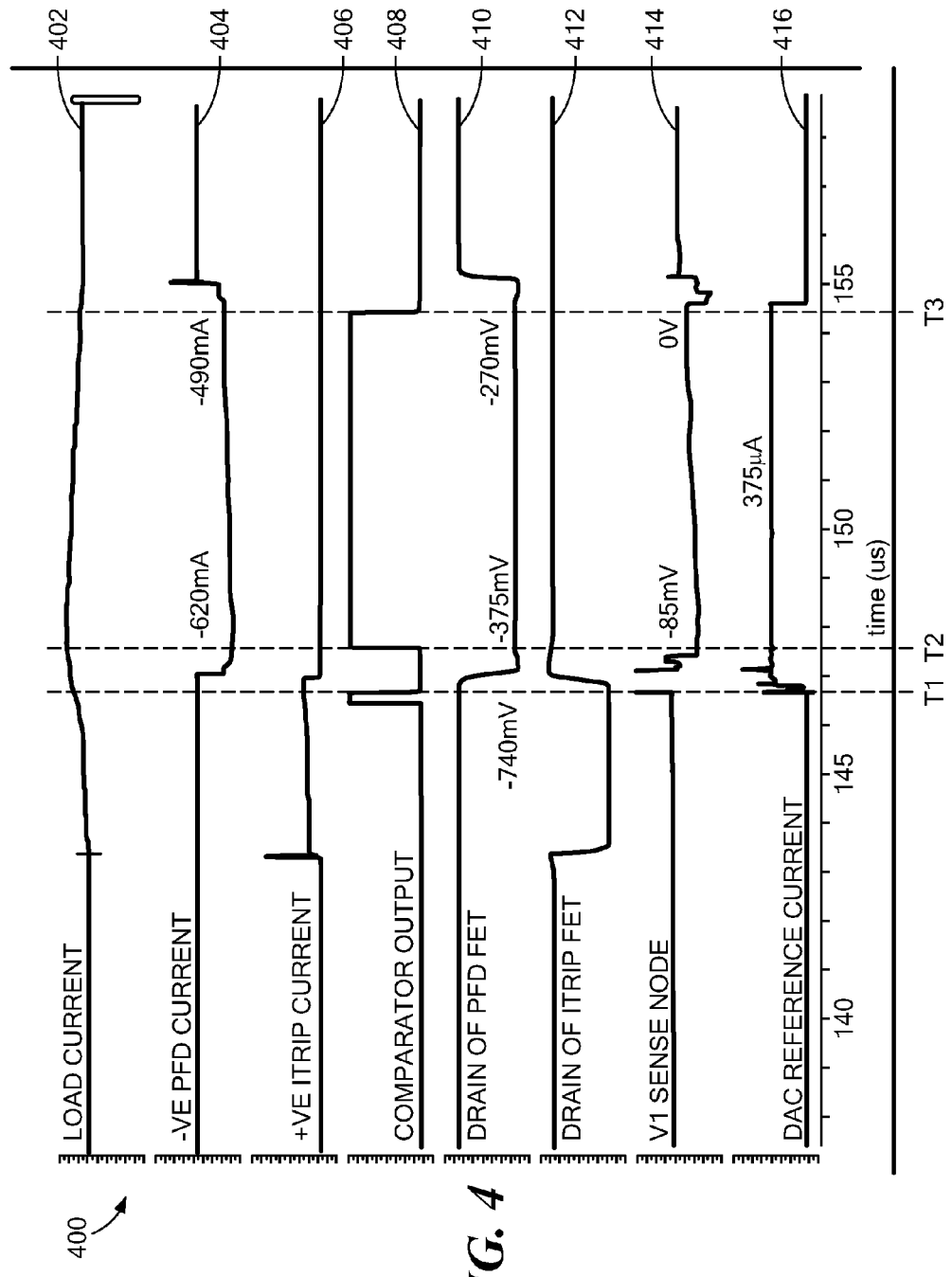
FIG. 4 is a graph of signals produced by a system for detecting reverse current.

Referring to FIG. 4, graph 400 includes examples of waveforms that may be generated by reverse current detector circuit 310 and low-side FET. Waveform 402 represents the current through motor winding 312. Waveform 404 represents the voltage at terminal 208 (the drain terminal of low-side-FET 202). Waveform 406 represents a current flowing through a low-side (e.g. FET 202) during the PWM on-time, i.e. when low side FET 202 is on and driving the load. Waveform 408 represents output signal 224a of comparator 218. Waveform 410 represents the voltage at the drain node of a low side FET (e.g. FET 202 or 112). Waveform 412 represents the voltage at the drain of a FET on the opposite side of the load. For example, if waveform 410 represents the voltage at the drain node of FET 112 in FIG. 1, then waveform 412 may represent the voltage at the drain node of FET. 114. Waveform 414 represents the voltage at the source node 306 of FET 302. Waveform 416 represents the output current of current source 304.

Referring to waveform 404, the current flowing through the low-side FET 202 while low-side FET 202 is on can be used to determine when to turn FET 202 off to stop driving the load. For example, while FET 202 is on, once the current reaches a predetermined threshold, the bridge may switch to a so-called off-time where the bridge is not actively driving the motor. During the off-time, FET 202 may be turned off, which may induce a fly-back current effect and cause reverse current to flow through FET 202, as described above.

In the example waveform shown, at or about time T1, FET 202 switches from an on state to an off state. Also at time T1, current source 304 turns on and drives a reverse current through FET 302, as shown by waveform 416. Between the times T1 and T2, a fly-back current from motor winding 312 drives the voltage at terminal 208 down, as shown by waveform 410. The voltage at source terminal 306 (at the input 220 of comparator 218) follows the voltage at terminal 208.

At time T2, the voltage at terminal 208 is low enough to allow reverse current to flow through transistor 202. Accordingly, at time T2, the voltage at source terminal 306 is below zero as shown by waveform 414. Comparator 218 then asserts signal 224a, as shown by waveform 408 at time T2.

Between times T2 and T3, the fly-back current dissipates, and the voltages at terminal 208 and source terminal 306 rise. This can be seen in the rising slopes of waveforms 410 and 414 between times T2 and T3. At time T3, the voltage at terminal 306 rises to zero volts and the comparator output transitions, indicating that the predetermined reverse current is no longer flowing through FET 202. It will be appreciated that the predetermined reverse current may have already ceased flowing prior to the transition of the comparator output due to comparator blanking or hysteresis and/or signal propagation delay, for example. In an embodiment, a fixed blank time is used which may prevent switching transients from falsely tripping the comparator.

In embodiments, a single reverse current detector circuit can be selectively coupled to two (or more) low-side FETs in an H-bridge in order to detect reverse current. For example, referring again to FIG. 1, when driving motor winding 124, typically only one of low-side FET 112 and 114 is off at a given time. A switch or series of switches can be used to couple reverse current detector 138 to low-side FET 112 while low-side FET 112 is off, and to couple reverse current detector 138 to low-side FET 114 when low-side FET 114 is off. Thus, a single reverse current detector 138 can be used to detect reverse current flowing through FET 112 and FET 114.

Figure 5:
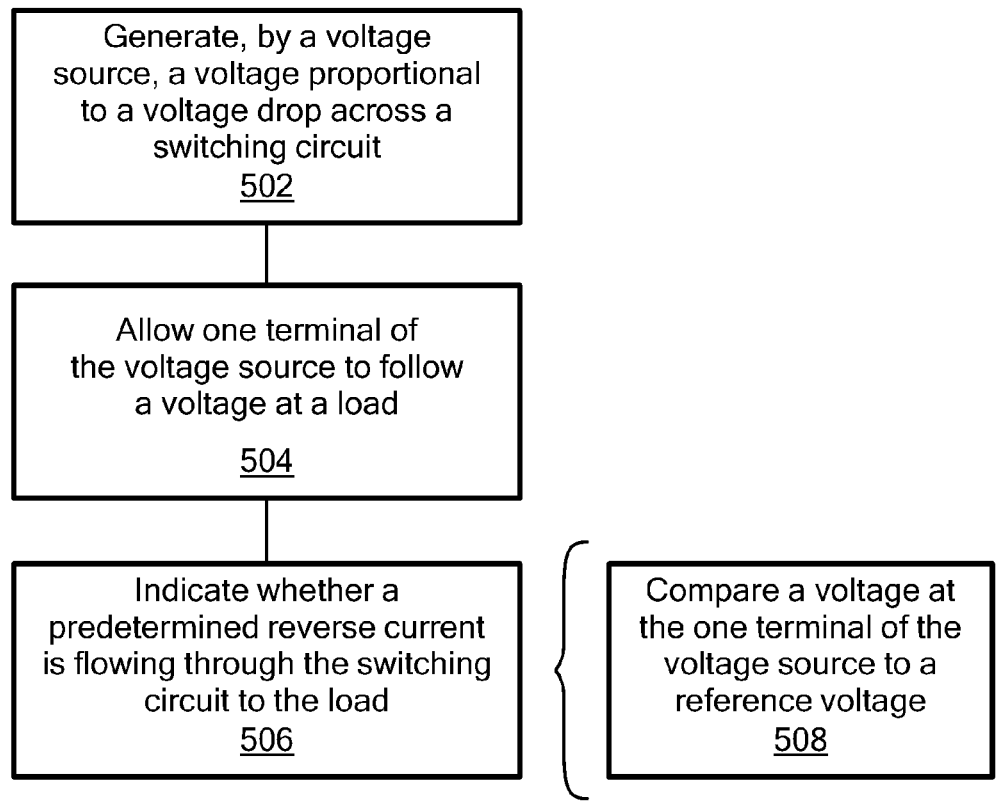
FIG. 5 is a flowchart of a method for detecting reverse current.

Referring to FIG. 5, a method 500 for detecting reverse current includes generating a voltage proportional to a voltage drop across a switching circuit in box 502. The voltage may be generated by a voltage source, a battery, etc. In an embodiment, the voltage may be generated by a current source 304 driving current through a FET 306, as shown in FIG. 3.

In box 504, one terminal of the voltage source is allowed to follow the voltage at a load. For example, in FIG. 3, the source terminal of FET 302 is tied to a high impedance input of comparator circuit 208. Thus, as Vds2 remains relatively constant, the voltage at source terminal 308 will follow any changes in the voltage at terminal 208, i.e. the voltage at motor 204.

In box 506, whether a predetermined reverse current is flowing through the switching circuit is indicated. For instance, when reverse current flows through FET 202 in FIG. 3, signal 224a is asserted by the comparator circuit 218 to indicate that the predetermined reverse current is flowing. In box 508, the system may indicate whether the reverse current is flowing by comparing a voltage at the one terminal of the voltage source (e.g. at source terminal 306) to a reference voltage (e.g. reference voltage 203, which may be a ground reference voltage).

Having described preferred embodiments, which serve to illustrate various concepts, structures and techniques, which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims. All references cited herein are hereby incorporated herein by reference in their entirety.

What is claimed is:

1. An apparatus comprising:
    a switching circuit coupled to a load and a reference node, the switching circuit capable of conducting a reverse current from the reference node to the load when a voltage at the load is lower than a voltage at the reference node;
    a voltage source having a first terminal coupled to the load, a second terminal configured to follow a voltage at the load, and produce a voltage indicative of a voltage drop across the switching circuit; and
    a comparator circuit coupled to compare a voltage at the second terminal of the voltage source to the voltage at the reference node and configured to indicate when the reverse current has a magnitude greater than a predetermined threshold.

2. The apparatus of claim 1 wherein the switching circuit comprises a transistor.

3. The apparatus of claim 2 wherein the transistor is a FET.

4. The apparatus of claim 2 wherein the voltage drop across the switching circuit is a voltage drop across a body diode of the transistor.

5. The apparatus of claim 2 wherein the transistor is a low-side transistor in motor driver circuit.

6. The apparatus of 1 wherein the voltage source comprises a sense transistor and a current source coupled to a source terminal of the sense transistor.

7. The apparatus of claim 6 wherein the current source is a digital-to-analog converter or is controlled by a digital-to-analog converter.

8. The apparatus of claim 6 wherein the produced voltage comprises a voltage drop across a body diode of the sense transistor.

9. The apparatus of claim 6 wherein a voltage at the source terminal of the transistor follows the voltage at the load.

10. The apparatus of claim 6 wherein a current conducted through the sense transistor is less than the reverse current.

11. The apparatus of claim 10 wherein the current conducted through the sense transistor is between about 1000 and about 1400 times less than the reverse current.

12. The apparatus of claim 1 wherein the produced voltage and the voltage drop across the switching circuit have substantially the same magnitude.

13. The apparatus of claim 1 wherein the comparator circuit is configured to indicate that the reverse current is flowing when the voltage at the second terminal of the voltage source is less than the voltage at the reference node.

14. The apparatus of claim 1 wherein the voltage drop across the switching circuit is a conduction threshold of the switching circuit, and the switching circuit is configured to conduct the reverse current when the voltage at the load is less than the voltage at the reference node minus the conduction threshold of the switching circuit when the switching circuit is in a non-conducting state.

15. The apparatus of claim 1 comprising at least one additional switching circuit and at least one additional voltage source.

16. The apparatus of claim 1 wherein the reference node is a ground node.

17. The apparatus of claim 1 wherein the voltage at the first terminal of the voltage source and the voltage at the second terminal of the voltage source both follow the voltage at the load.

18. The apparatus of claim 1 wherein the voltage is proportional to a voltage drop across the switching circuit.

19. A motor driver circuit comprising:
    a low-side transistor coupled between a load and a reference node, the low-side transistor capable of conducting a reverse current from the reference node to the load when a voltage at the load is lower than a voltage at the reference node;

a voltage source having a first terminal coupled to the load, a second terminal configured to follow a voltage at the load, and produce a voltage indicative of a voltage drop across a body diode of the low-side transistor; and a comparator circuit coupled to compare a voltage at the second terminal of the voltage source to the voltage at the reference node and configured to indicate when the reverse current is flowing.

20. The motor driver circuit of claim 19 wherein the load comprises a motor.

21. The motor driver circuit of claim 19 wherein the voltage source comprises a sense transistor and a current source coupled to a source terminal of the sense transistor to provide a current through the sense transistor, and the produced voltage comprises a voltage drop across a body diode of the sense transistor.

22. The motor driver circuit of claim 21 wherein the low-side transistor and the sense transistor are formed on a same substrate.

23. The motor driver circuit of claim 22 wherein the sense transistor is smaller than the low-side transistor, and the current through the second transistor is smaller than the reverse current through the low-side transistor.

24. The motor driver circuit of claim 23 wherein the current through the second transistor is between about 1000 and about 1400 times smaller than the reverse current through the low-side transistor.

25. The motor driver circuit of claim 20 wherein the current source comprises a digital-to-analog converter.

26. A motor driver circuit comprising:
a motor; and
a switched bridge for driving the motor, the switched bridge comprising:
a low-side transistor having a gate terminal coupled to a control circuit, a drain terminal coupled to at least one coil of the motor, and a source terminal coupled to a reference node;
a sense transistor having a gate terminal coupled to the gate terminal of the low-side transistor, a drain terminal coupled to the at least one coil of the motor, and a source terminal;
a current source coupled to the source terminal of the sense transistor to produce a voltage across a body diode of the sense transistor and to allow a voltage at the source terminal of the sense transistor to follow a voltage at the at least one coil of the motor, wherein the source terminal of the sense transistor is configured to produce a voltage indicative of a voltage drop across a body diode of the low-side transistor; and
a comparator circuit coupled to compare the voltage at the source terminal of the sense transistor to a voltage at the reference node and to indicate when a predetermined reverse current is flowing from the reference node to the at least one coil of the motor through the low-side transistor by indicating when the voltage at the source terminal of the sense transistor is less than the voltage at the reference node.

27. The motor driver circuit of claim 26 wherein the low-side transistor is a FET.

28. The motor driver circuit of claim 27 wherein the sense transistor is a FET that is smaller than the low-side transistor by a predetermined scale factor.

29. The motor driver of claim 26 wherein the switched bridge is an H-bridge or a half-bridge.

30. A method comprising:
generating, by a voltage source, a voltage that is indicative of a voltage drop across a switching circuit that is coupled to a load and a reference node;
allowing at least one terminal of the voltage source to follow a voltage at the load; and
indicating whether a predetermined reverse current is flowing through the switching circuit by comparing a voltage at the one terminal of the voltage source to a voltage at the reference node.

31. The method of claim 30 wherein generating the voltage comprises generating a voltage that is a substantially equal to the voltage drop across the switching circuit.

32. The method of claim 30 wherein generating, by the voltage source, a voltage that is indicative of a voltage drop across the switching circuit comprises generating a voltage that is proportional to the voltage drop across the switching circuit.

* * * * *

UNITED STATES PATENT AND TRADEMARK OFFICE
CERTIFICATE OF CORRECTION

PATENT NO. : 9,735,773 B2
APPLICATION NO. : 14/264522
DATED : August 15, 2017
INVENTOR(S) : James McIntosh et al.

It is certified that error appears in the above-identified patent and that said Letters Patent is hereby corrected as shown below:

In the Specification

Column 6, Line 57, delete "or by be" and replace with --or may be--

Column 8, Lines 9-10, delete "current through flowing through body" and replace with --current flowing through body--

Column 8, Line 29, delete "and low-side FET" and replace with --and low-side FET 202--

Column 9, Line 26, delete "a method 500 for" and replace with --a method for--

In the Claims

Column 10, Line 19, Claim 5 delete "transistor in motor driver circuit" and replace with --transistor in a motor driver circuit--

Column 12, Line 35, Claim 31 delete "that is a substantially" and replace with --that is substantially--

Signed and Sealed this
Twenty-fourth Day of April, 2018

Andrei Iancu
*Director of the United States Patent and Trademark Office*